(12) United States Patent
do Canto

(10) Patent No.: US 6,495,230 B1
(45) Date of Patent: Dec. 17, 2002

(54) FILM-BASED BANDAGE MATERIAL

(75) Inventor: Fabricio do Canto, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/392,431

(22) Filed: Sep. 9, 1999

(30) Foreign Application Priority Data

Sep. 11, 1998 (DE) .......................................... 198 41 550

(51) Int. Cl.$^7$ ................................................. A61F 13/02
(52) U.S. Cl. ..................... 428/41.8; 428/40.1; 428/42.1; 428/42.2; 428/192; 428/194; 602/54; 602/55; 602/58; 602/59; 602/77
(58) Field of Search ............................... 428/40.1, 42.1, 428/42.2, 192, 194, 41.8; 602/54, 55, 58, 59, 77

(56) References Cited

U.S. PATENT DOCUMENTS

| 3,645,835 A | 2/1972 | Hodgson | 161/146 |
|---|---|---|---|
| 4,024,312 A | 5/1977 | Korpman | |
| 4,600,001 A | 7/1986 | Gilman | 128/156 |

FOREIGN PATENT DOCUMENTS

| DE | 2728346 | 1/1978 |
|---|---|---|
| DE | 38 09 539 A1 | 10/1989 |
| DE | 4026755 A1 | 2/1992 |
| DE | 43 14 834 A1 | 11/1994 |
| DE | 4314834 C2 | 11/1994 |
| DE | 195 31 696 | 8/1995 |
| DE | 19531696 | 3/1997 |
| DE | 693 05 779 T2 | 5/1997 |
| EP | 0 066 899 A2 | 12/1982 |
| EP | 0 747 027 A2 | 12/1996 |
| EP | 0 845 515 A2 | 6/1998 |
| EP | 0 922 739 A1 | 6/1999 |
| FR | 2 711 056 A1 | 4/1995 |
| WO | 90/01915 A2 | 3/1990 |
| WO | 9211333 | 7/1992 |
| WO | 92/11333 A1 | 7/1992 |
| WO | 9506691 | 3/1995 |
| WO | 95/06691 A1 | 3/1995 |

OTHER PUBLICATIONS

Opsite®–Folie der Firma B. Braun–Dexon GmbH Melsungen (Prospekt), dated Jun. 3, 1976.
Derwent Abstract of DE 43 14 834 (No Date).
Derwent Abstract of DE 40 26 755 (No Date).

*Primary Examiner*—Nasser Ahmad
(74) *Attorney, Agent, or Firm*—Norris McLaughlin & Marcus

(57) ABSTRACT

Film-based bandage material, the film consisting of polyurethane, being treated so as to be self-adhesive on one side and having at least one non-adhesive grip tab formed onto it, so that following application the bandage material can be detached from the substrate by pulling on the grip tab in the direction of the bond plane.

3 Claims, 1 Drawing Sheet

FILM-BASED BANDAGE MATERIAL

BACKGROUND OF THE INVENTION

The invention relates to a film-based bandage material which is treated so as to be self-adhesive on one side and formed onto which there is at least one non-adhesive grip tab.

Adhesively coated backing systems which de-adhere when the backing is pulled are known. They are generally based on elastic systems, which in many cases constitute laminates.

DE-A 27 28 346 describes an adhesive tape of this kind which consists of an extensible film and an adhesive composition based on A-B-A block copolymers. The completely adhering laminate can easily be detached from the substrate by stretching. The adhesive composition is applied over the whole area. No grip tab is provided for stretching the bonded tape.

DE-A 195 31 696 describes an adhesive-tape laminate which is produced from an extensible backing and an acrylate adhesive composition.

WO 95/06691 discloses a redetachable adhesive tape whose backing material comprises a foam.

WO 92/11333 describes a system which can be removed nondestructively and which possesses a high tensile strength.

DE 40 26 755 A1 discloses a film-based bandage material which is covered on one side with a support material which is the same size as the film and has at least one grip strip, and on the other side is provided with a self-adhesive layer. The grip strips for removing the backing material are arranged within its peripheral limits. Preferably, only one grip strip is attached to the backing material.

DE 43 14 834 C2 discloses a film-based bandage material which is covered on one side with a backing material which is the same size as the film and has at least one grip strip, and on the other side is provided with a self-adhesive layer. The grip strips for removing the backing material are arranged within its peripheral limits. Preferably, only one grip strip is attached to the backing material.

With both of the abovementioned bandages the problem arises, following application, of how to detach them from the skin, since they are bonded over their entire area. The patient is therefore forced to lift up a section of the film in the marginal region from the skin by inserting a fingernail, for example, under the film. This procedure firstly is very unsatisfactory and secondly can be painful, especially in the case of relatively large wounds and the irritated skin that accompanies them.

EP 0 747 027 A2 discloses an adhesive tape section consisting of an adhesive composition lined on one side with a thin cover film. On the opposite side there are two further sections of a film on the adhesive composition, so producing, in the marginal region, two grip tabs by means of which the adhesive tape section can be detached from the substrate by pulling in the bond plane.

The object of the invention is to avoid the disadvantages known from the prior art and to provide a film-based bandage material which is treated so as to be self-adhesive on one side and which can be detached again from the skin, following application, easily and painlessly by stretching.

This object is achieved by a film-based bandage material as set out in the main claim. The subclaims relate to advantageous developments of the bandage material.

SUMMARY OF THE INVENTION

Accordingly, the invention proposes a film-based bandage material in which the film is comprised of polyurethane, is treated so as to be self-adhesive on one side and has at least one non-adhesive grip tab formed onto it, so that following application the bandage material can be detached from the substrate by pulling on the grip tab in the direction of the bond plane.

The bandage film itself is comprised of elastic, thermoplastic polyurethanes, as described in DE-C 19 34 710 (=U.S. Pat. No. 3,645,835), which feature good skin compatibility and also permeability to oxygen and water vapour. Aliphatic polyester urethanes have proved to be particularly advantageous.

A preferred film is about 30 to 40 $\mu$m thick, transparent, has an elongation at break of more than 450% and a water vapour permeability of more than 500 g/m$^2$ in 24 h at 38° C. and 95% relative humidity in accordance with DAB [German Pharmacopoeia].

The thickness of this film can be from about 15 to 300, preferably from 15 to 80 $\mu$m, the weight, accordingly, from about 15 to 350 g/m$^2$, preferably from 15 to 100 g/m$^2$, the maximum tensile force in the longitudinal direction from about 5 to 100 N/cm, preferably from 2 to 40 N/cm, and the elongation at break in the longitudinal direction from about 100 to 1000%.

The adhesion of the film to the backing material, which need only be low (from about 0.01 to 0.5 N/cm, preferably from 0.01 to 0.05 N/cm), is preferably brought about by producing the thin film directly on the backing by casting, knifecoating, extrusion or other known methods of producing films. If necessary, the backing material can be roughened on the coating side or given some other adhesion-promoting treatment. An adhesion-promoting coating may also be advantageous.

What is important in this context is that the adhesion of the finished bandage to the skin is substantially stronger than the adhesion of the backing to the film.

The grip tabs are present, in particular, at the marginal region of the film, so as not to complicate further the production of the bandage material. Preferably, only one grip tab is present. By pulling on the grip tab essentially in the direction of the bond plane, the film becomes stretched and at the same time detaches itself from the underlying skin with, surprisingly, no pain.

In order to minimize the amount of sealing paper and/or other packaging material employed in the case of individual punched plasters, the grip tab can be folded so that it lies on the side of the film that is not coated with the adhesive.

In one preferred embodiment the film is covered on one side with a backing material which has the same size as the film and possesses at least one grip strip.

The backing material, which has a supporting action for the film, remains on the film during application of the bandage and is not removed until afterwards; it is preferably comprised of a polyethylene film about 80 $\mu$m thick which is slightly roughened on its side facing the film and thus has a matt but still translucent appearance.

It is also possible to use other films made, for example, of polypropylene, polyester of PVC, or suitable thin, coated paper, so long as they are sufficiently pliable not to interfere during application of the bandage.

Their technical data can be within the following ranges:

| | |
|---|---|
| Thickness: | 30–300 µm |
| Weight: | 30–350 g/m$^2$ |
| Maximum tensile force, longitudinal: | 5–100 N/cm |
| Elongation at break, longitudinal: | 10–3000% |

Their surface facing the film can be smooth, roughened or slightly embossed.

The grip strips are preferably comprised of an LDPE (low-density polyethylene) film 80 µm thick. So as to be easily visible, it is coloured—blue, for example—and for improved grip is provided with matt embossing on the outside.

Instead of this film, it is also possible to use other materials, such as HDPE, polypropylene, PVC, PU or polyester films, and also nonwovens, paper or wovens, so long as they are again sufficiently flexible and pliable.

Depending on the material, the thickness can be between 10 and 300 µm, the weight, accordingly, from 10 to 350 g/m$^2$. The surface can be matt, glossy, rough, smooth or printed. The maximum tensile force in the longitudinal direction can vary between about 3 and 100 N/cm and the resultant elongation can be between 5 and 500%.

The grip strips can be attached to the backing material in a wide variety of ways depending on the material and processing machines, but preferably by adhesive bonding or welding. Adhesive bonding takes place, for example, by introducing a strip of a double-sided adhesive tape between the backing material and the grip strips in the region to be bonded, or a coating of adhesive composition consisting of a hot-melt or self-adhesive composition of a solvent or dispersion.

The grip strips may extend over the entire length or width of the bandage, and may also finish flush with at least one side edge.

The grip strips may be arranged within the peripheral limit of the bandage material or else may extend beyond the edge of the bandage material.

The grip strips are preferably made of an LDPE film.

Advantageously, only one grip strip is attached to the backing material. In this case it has been found advantageous for the grip strip to be fastened to the backing material in a narrow stripelike marginal region and to have, to the left or right of this region, on one side, a free grip region of at least about 5 mm, or for the grip strip to be fastened to the backing material in a narrow central stripelike region and on either side thereof to have a free grip region of at least about 5 mm in width.

The adhesive layer on the film preferably has, for example, a bond strength to steel of from about 2 to 4 N/cm; for the measurement, the test material must be reinforced on the reverse with a non-elastic adhesive film, since the film is highly extensible. The measurement itself was carried out in accordance with DAB 9.

The bandage material can be used as such, but it is also possible for a conventional, absorbent wound pad, which is smaller than the area of adhesion, to be applied additionally in an appropriate width in the centre, so that the material can be used directly as a wound bandage (dressing). A bandage of this kind with all-round adhesive bonding is particularly advantageous since it is germ-proof and water-resistant.

On its side which is provided with the self-adhesive coating and which later faces the skin, the bandage material of the invention is covered over its entire width, until used, with an anti-adhesive backing material, such as siliconized paper. This protects the self-adhesive layer, comprising a highly skin-compatible adhesive composition based, for example, on acrylate, which has preferably been applied by the transfer method, and also stabilizes the product as a whole. The cover can be formed conventionally in one piece or, preferably, in two parts.

In one preferred embodiment the bondage material, at a tensile load of 10 N/cm, exhibits an extension of more than 10% to 3000%, with particular preference from 20% to 1000%.

DESCRIPTION OF PREFERRED EMBODIMENT

Figure 1:
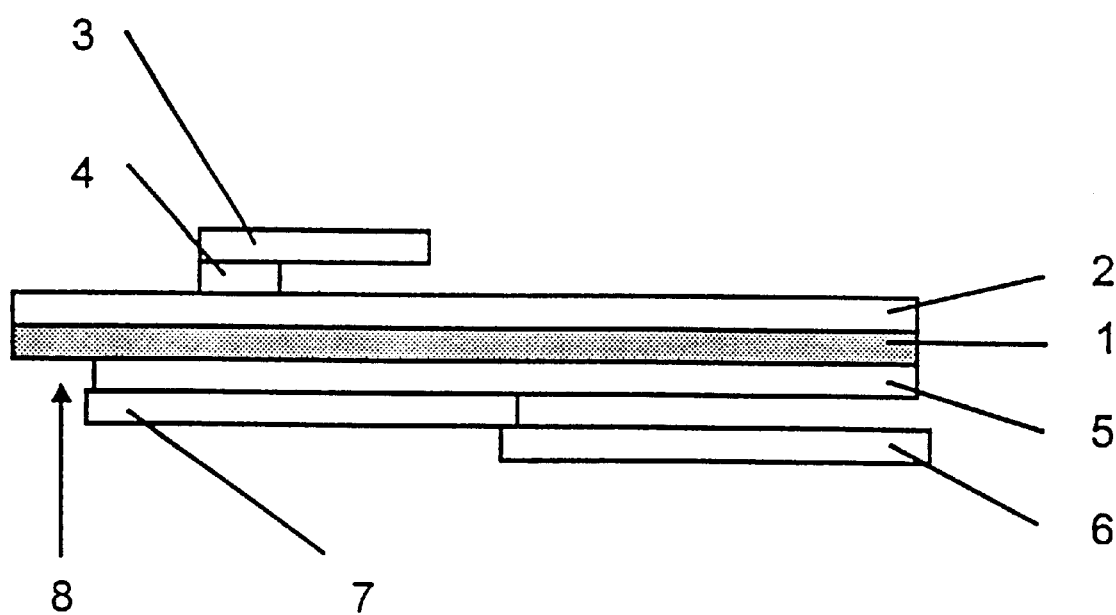
FIG. 1 shows the bandage material of the invention with enlarged thicknesses of the layers by way of example. In the figure, (1) denotes the film,
(2) denotes the backing,
(3) denotes the grip strip,
(4) denotes an adhesive layer for attaching the grip strip to the backing,
(5) denotes the self-adhesive layer,
(6) and (7) denote the protective covers for the self-adhesive layer, and
(8) denotes the grip tab formed onto the film.

In the text below, a number of examples are used to depict particularly advantageous embodiments of the bandage material without wishing thereby unnecessarily to restrict the invention.

EXAMPLE 1

The bandage material of the invention is an anionic aliphatic polyester polyurethane dispersion film (Impranil® DLN Dispersion from Bayer) measuring 50×50 mm. The film has a thickness of 0.1 mm.

The film is coated on one side with a skin-compatible adhesive layer based on crosslinked polyacrylic acid derivatives.

After adhesive bonding, the bandage material is to be removed from the skin by pulling on an adhesive-free grip tab which is present on one of the edges of the film and measures 10×50 mm.

The pulling action results in the disbanding of the film, so that the bandage material can be removed painlessly.

EXAMPLE 2

The bandage material of the invention is formed, in the same way as in Example 1, by a polyurethane gel "Cutinova thin"® from Beiersdorf AG which is additionally covered with the polyester polyurethane dispersion film (Impranil® DLN Dispersion from Bayer) from Example 1.

This wound bandage also permits painless removal following application, by pulling on an adhesive-free grip tab which is present on one of the edges of the film and measures 10×50 mm.

I claim:

1. Film-based bandage material, comprising a polyurethane film which, at a tensile load of 10 N/cm exhibits an extension of from more than 10% to 3000%, one side of which is treated to be self-adhesive and having at least one non-adhesive grip tab formed onto it, the other side of said film being covered with a backing material having the same size as the film and which has at least one grip strip, so that following application to a substrate the bandage material can be detached from the substrate by pulling on the grip tab in the direction of the bond plane.

2. Bandage material according to claim 1, wherein on the adhesive side there is a wound pad which is smaller than the area of adhesion.

3. Bandage material according to claim 1, wherein the self-adhesive side is provided with a removable protective cover.

* * * * *